(12) United States Patent
Nah et al.

(10) Patent No.: US 7,883,723 B2
(45) Date of Patent: Feb. 8, 2011

(54) WATER SOLUBLE CHITOSAN NANOPARTICLE FOR DELIVERING AN ANTICANCER AGENT AND PREPARING METHOD THEREOF

(75) Inventors: Jae-Woon Nah, #101-501 Jeongwon NexVill Apt., 512 Joguk-dong, Sooncheon-shi, Jeolanam-do 540-963 (KR); Teok Rae Jung, #4 Gowon Building, 20-19 Yangjae-dong, Seocho-gu, Seoul 135-888 (KR); Mi-Kyeong Jang, #428 Dramacity Mokryeon Maeul, 980-1 15/5 Gagok-dong, Sooncheon-shi, Jeolanam-do 540-080 (KR); Young-Il Jeong, Gwangju-shi (KR)

(73) Assignees: Jae-Woon Nah, Sooncheon-shi, Jeolanam-do (KR); Teok Rae Jung, Seoul (KR); Mi-Kyeong Jang, Sooncheon-shi, Jeolanam-do (KR)

( * ) Notice: Subject to any disclaimer, the term of this patent is extended or adjusted under 35 U.S.C. 154(b) by 1105 days.

(21) Appl. No.: 11/128,297

(22) Filed: May 13, 2005

(65) Prior Publication Data
US 2006/0013885 A1 Jan. 19, 2006

(30) Foreign Application Priority Data
Jul. 16, 2004 (KR) .................. 10-2004-0055649

(51) Int. Cl.
*A01N 25/02* (2006.01)
*A01N 43/02* (2006.01)
*A61K 9/14* (2006.01)
*A61K 9/16* (2006.01)
*A61K 31/21* (2006.01)
*C08B 37/08* (2006.01)

(52) U.S. Cl. .................. 424/493; 424/489; 424/498; 536/20; 514/449; 514/510

(58) Field of Classification Search .................. None
See application file for complete search history.

(56) References Cited

U.S. PATENT DOCUMENTS

| | | | |
|---|---|---|---|
| 5,439,686 | A | 8/1995 | Desai et al. |
| 5,498,421 | A | 3/1996 | Grinstaff et al. |
| 5,560,933 | A | 10/1996 | Soon-Shiong et al. |
| 5,916,596 | A | 6/1999 | Desai et al. |
| 6,096,331 | A | 8/2000 | Desai et al. |
| 6,322,817 | B1 * | 11/2001 | Maitra et al. .................. 424/489 |
| 6,566,516 | B1 * | 5/2003 | Sunamoto et al. ....... 536/123.12 |
| 6,602,952 | B1 * | 8/2003 | Bentley et al. .................. 536/20 |
| 2003/0157161 | A1 * | 8/2003 | Hunter et al. ................ 424/450 |

FOREIGN PATENT DOCUMENTS

| | | |
|---|---|---|
| WO | 94/18954 A1 | 9/1994 |
| WO | 98/14174 A1 | 4/1998 |
| WO | 99/00113 A1 | 1/1999 |

OTHER PUBLICATIONS

Sashiwa et.al, chemical modification of chitosan. Part 15: Synthesis of novel chitosan derivatives by substitution of hydrophilic amine using N-carboxyethylchitosan ethyl ester as an intermediate, Carbohydrate Research, vol. 338, issue 6, pp. 557-561, 2003.*
S. Mitra et al, Tumor targeted delivery of encapsulated dextran-doxorubicin conjugate using chitosan nanoparticle as carrier, Journal of controlled Release, 74 (2001)317-323.*
Jang et al, Bull. Korean. Chem. Soc., 2003, vol. 24, No. 9 pp. 1303-1307.*
Jang, M., et al., "The Investigation on Characterization of Chitosan Nanoparticle Modified with Hydrophobic Moiety", 2002, Applied Chemistry, 6(1), pp. 19-22.*
Miwa, A., et al., "Development of Novel Chitosan Derivatives as Micellar Carriers of Taxol", *Pharmaceutical Research*, vol. 15, No. 12, pp. 1844-1850, (1998).
Paul, W., et al., "Chitosan, a drug carrier for the 21$^{st}$ century: a review", *S.T.P. Pharma Sciences*, vol. 10, No. 1, pp. 5-22, (2000).

* cited by examiner

*Primary Examiner*—Michael G Hartley
*Assistant Examiner*—Lance Rider
(74) *Attorney, Agent, or Firm*—The Nath Law Group; Joshua B. Goldberg; Tanya E. Harkins

(57) ABSTRACT

The present invention relates to a water soluble chitosan nanoparticle (WSC-NP) for delivering an anticancer agent and a preparing method thereof, more precisely, a water soluble chitosan nanoparticle for delivering an anticancer agent which has function of targeting on a wanted area by introducing a functional group in the location of highly reactive amine group and becomes an excellent gene carrier with the use of water soluble chitosan since the water soluble chitosan itself can combined with DNA having a negative electric charge(−) owing to the very strong positive electric charge(+) of its amine group, and a preparing method thereof. Therefore, a water-soluble chitosan nanoparticle for delivering an anticancer agent of the present invention can effectively envelope paclitaxel by introducing hydrophilic and hydrophobic groups in the position of highly reactive amine group of the water-soluble chitosan. A water soluble chitosan nanopaclitaxel prepared as the above has an excellent re-dispersion force, after freeze-drying, in distilled water and has an outstanding anticancer effect with its accumulation in tumor cells greater than that of the other anticancer agent carriers.

2 Claims, 15 Drawing Sheets

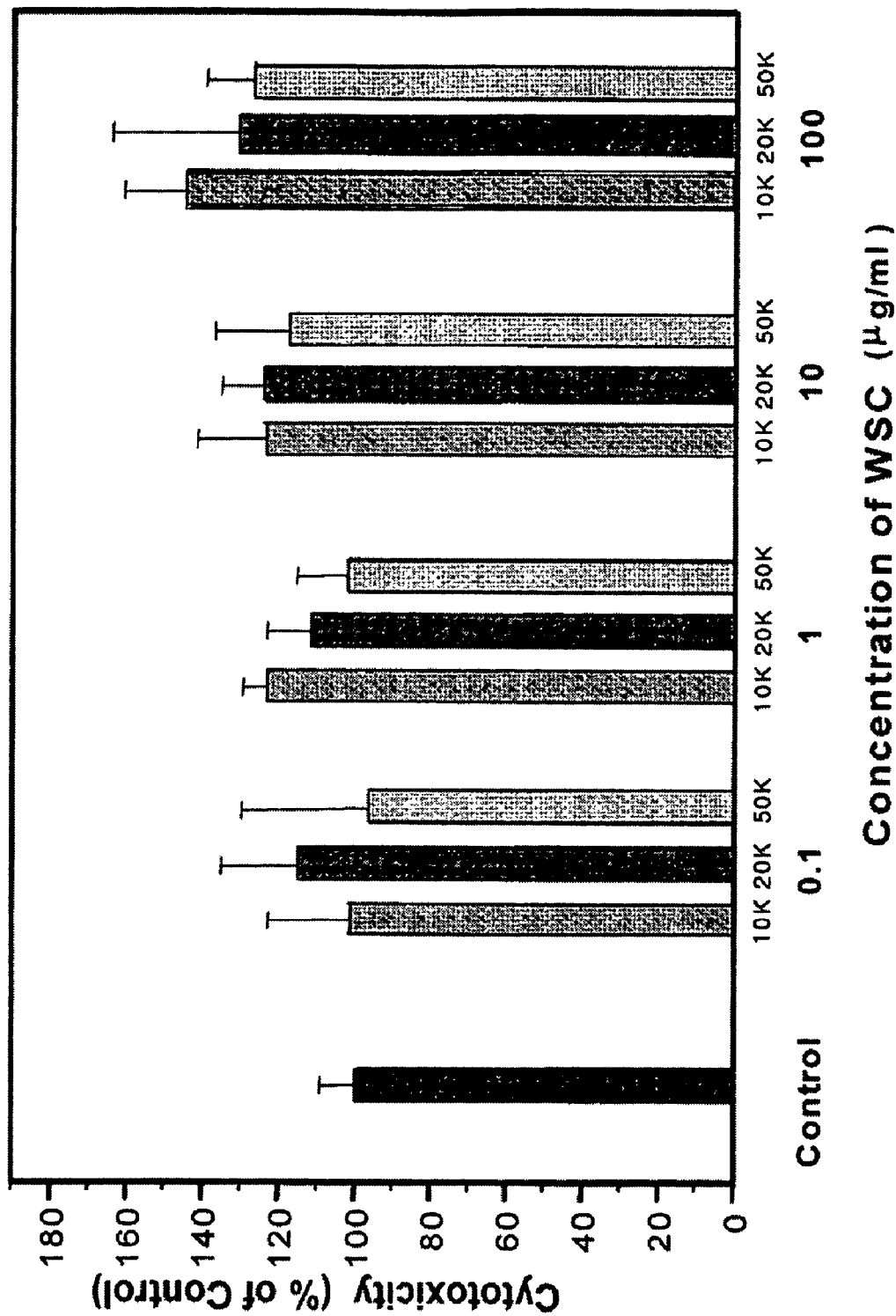

FIGURE 4
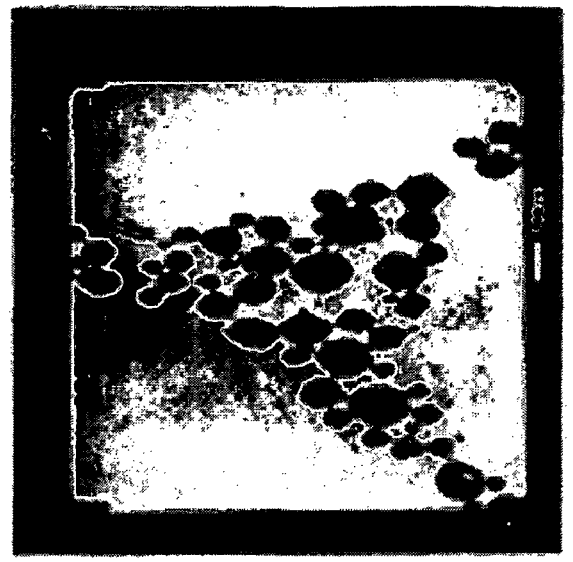
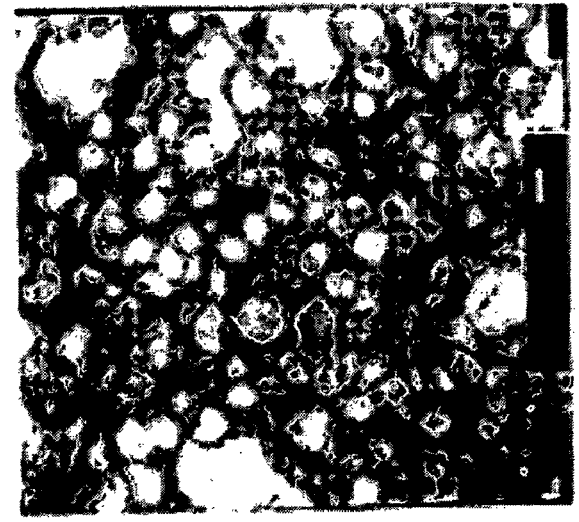

WATER SOLUBLE CHITOSAN NANOPARTICLE FOR DELIVERING AN ANTICANCER AGENT AND PREPARING METHOD THEREOF

BACKGROUND OF THE INVENTION

1. Field of the Invention

The present invention relates to a water soluble chitosan nanoparticle (WSC-NP) for delivering an anticancer agent and a preparing method thereof, more precisely, a water soluble chitosan nanoparticle for delivering an anticancer agent which has function of targeting on a wanted area by introducing a functional group in the location of highly reactive amine group and becomes an excellent gene carrier with the use of water soluble chitosan (WSC) since the water soluble chitosan itself can combined with DNA having a negative electric charge(−) owing to the very strong positive electric charge(+) of its amine group, and a preparing method thereof.

2. Description of the Prior Art

Chitosan is formed by β-1,4 bond of pyranose monomers of glucosamine, having over 5,000 residues of glucosamine. Its molecular weight is over one million. As a biopolymer belonging to polysaccharide having polycations, chitosan is extracted from aquatic products such as *Crustacea* like crab or shrimp and a squid. It has a similar molecular structure to that of cellulose, a kind of polysaccharide, indicating that it has an excellent biocompatibility without rejection by immune reaction. So, chitosan has been widely used in medical industry and recently attested by FDA, U.S.A. to be safe food. Thus, chitosan is expected to be a relevant material applicable to bioindustry and biomedical industry in the $21^{st}$ century.

In particular, chitosan having a molecular weight ranging from 20,000 to 100,000 is known to have very strong physiological activities, so the chitosan can be applied to the production of health food, food and beverages, cosmetics, sanitation and medical supplies.

Although the above promising characteristics of chitosan, it has not been applied successfully to the bioindustry since it is an insoluble in water owing to the strong hydrogen bond with neighboring molecules and organic acids including lactic acid, acetic acid, propionic acid, formic acid, ascorbic acid and tartaric acid, and inorganic acids including hydrochloric acid, nitric acid and sulfuric acid had to be used to dissolve chitosan. In order to overcome the problem, the present inventors have developed a water-soluble chitosan and applied for a patent (Korea Patent Application Nos. 2001-0059282 and 2001-0070052).

In the above patents, a preparing method for a pure water soluble free amine chitosan having a molecular weight ranging 1,000~100,000 Da was reported, which includes the steps of 1) organic or inorganic acid salt solution of chitosan oligosaccharide is treated with trialkyl amine, 2) an organic solvent is added to the above solution to separate organic or inorganic acid linked with chitosan oligosaccharide which becomes trialcohol amine salt, and then, recover the chitosan oligosaccharide without organic or inorganic salt, 3) the solution of chitosan oligosaccharide without acid is treated with inorganic acid and purified by activated carbon/ion exchange resin column, resulting in a pure water soluble free amine chitosan having a molecular weight of 1,000~100,000 Da.

Although paclitaxel, attested by FDA, U.S.A. in 1992, has a very excellent anticancer activity comparing to other conventional anticancer agents, it has a serious problem of side effects resulted from that it has to be dispersed in a mixed solution of cremophore EL (polyethoxylated oil) and ethanol (50:50) to be used as an injection because paclitaxel is hydrophobic so that it is not dispersed in water at all.

Because of insolubility in water, paclitaxel, a natural material having an anticancer activity, has limitation in use as an injection. Therefore, various systems have been proposed to make injection of paclitaxel possible. For example, human serum albumin (HSA) which is biodegradable and strongly bound to paclitaxel was combined with paclitaxel, followed by sonication, high-pressure homogenization and microfluidization according to a conventional method, resulting in an emulsion applicable as an injection.

Applicable injections prepared by combination of paclitaxel produced by VivoRx Pharmaceuticals, Inc. by taking advantage of sonication skill providing an average particle size of under 10 μm and human serum albumin particles were reported in U.S. Pat. Nos. 5,439,686, 5,498,421, 5,560,933 and WO 94/18954. However, the preparing methods reported in the above patents cannot be used on a large industrial scale. Moreover, the particles resulted from the above methods are too big to be administered to a patient.

Other reports concerning paclitaxel having an average size of under 0.2 μm obtained from dissolving freeze-dried powder in sterilized 0.9% NaCl solution and sterilized human serum albumin nano-emulsion have been made in U.S. Pat. Nos. 5,916,596, 6,096,331, WO 98/14174 and WO 99/00113 as well. According to the above reports, particles in nano-emulsion obtained through high-pressure homogenization are uniform in size and nanoparticle precipitate is not formed as time passes, indicating the stability of nano-emulsion. However, paclitaxel suspension prepared by mixing with human serum albumin is not available as an injection on industrial scale, yet.

Thus, the present inventors have studied on a method to use chitosan as a paclitaxel carrier which is applicable to medical industry successfully because chitosan has excellent biocompatibility without rejection by immune reaction as being administered, and have completed this invention by establishing the method.

SUMMARY OF THE INVENTION

It is an object of the invention to provide a water soluble chitosan nanoparticle which makes possible to use highly water soluble chitosan having free amine group as a paclitaxel carrier and a preparation method of the same.

In order to achieve the above object, the present invention provides a water soluble chitosan nanoparticle for effective delivering an anticancer agent and a preparation method for the same, in which a water soluble chitosan is used as a basic component for an anticancer agent carrier, a water soluble chitosan itself becomes an outstanding gene carrier by being combined with a DNA having a negative charge (−) owing to the amine group of chitosan having a very strong positive charge (+), and the carrier is given function of targeting on a wanted area by introducing a functional group in highly reactive free amine group.

BRIEF DESCRIPTION OF THE DRAWINGS

The application of the preferred embodiments of the present invention is best understood with reference to the accompanying drawings, wherein:

FIG. 1 is a graph showing the MTT test results of a WSC,

FIG. 4 and FIG. 5 are photographs showing the surface of WSC-NP of the present invention taken by TEM and AFM.

DETAILED DESCRIPTION OF THE PREFERRED EMBODIMENTS

Figure 2A:
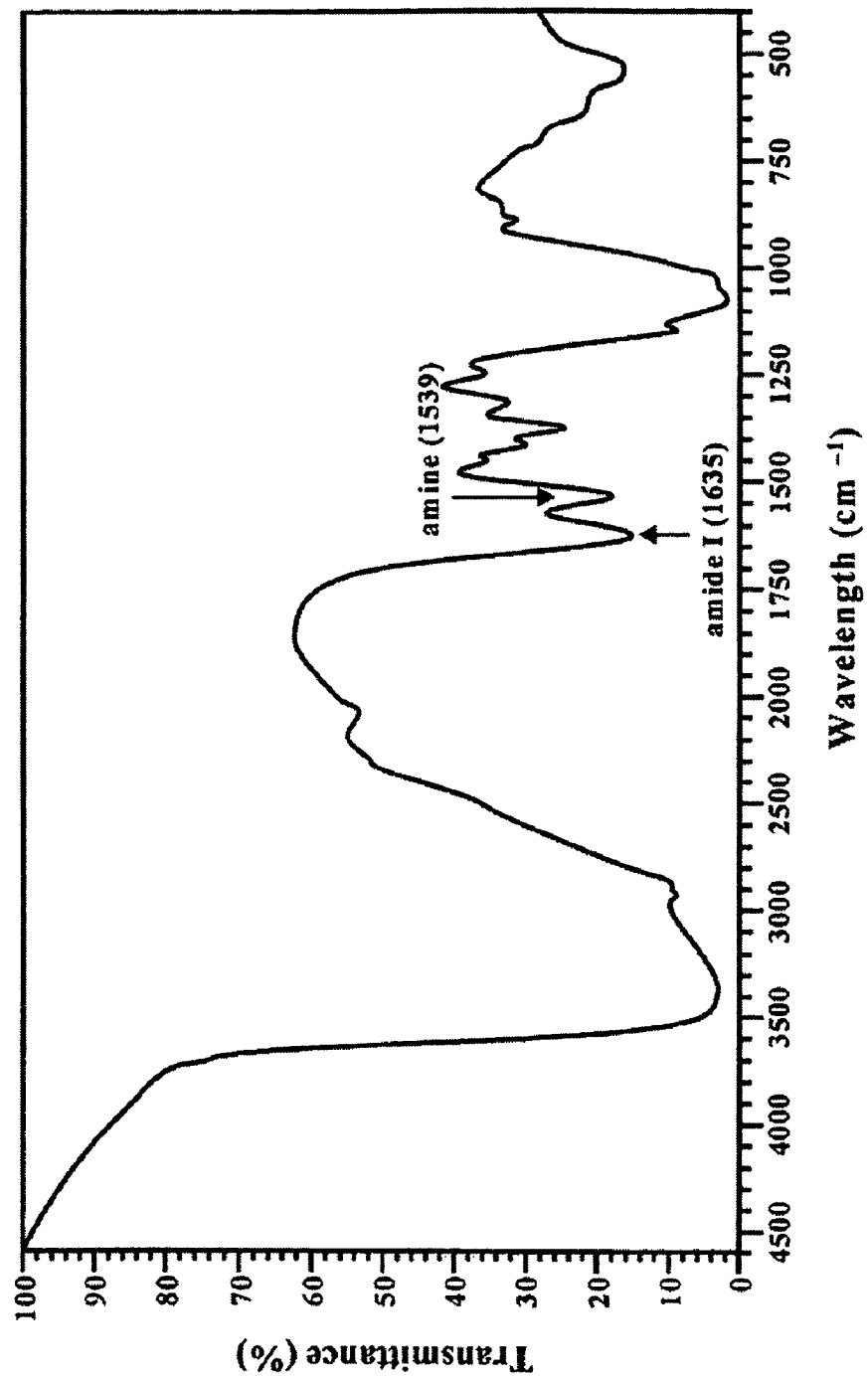
FIGS. 2A and 2B are a set of graphs showing the FT-IR spectrum of a WSC conjugated with MEPG p-NP.

Hereinafter, the present invention will be described in more detail.

The present invention provides a water-soluble chitosan nanoparticle (WSC-NP) for delivering an anticancer agent that is prepared by introducing cholesterol as a hydrophobic group and methoxy poly (ethylene glycol) as a hydrophobic group.

The introduced cholesteryl chloroformate seals paclitaxel, a hydrophobic medicine, to be carried, and MPEG increases solubility of the cholesterol, resulting in making paclitaxel to be circulated in blood for a long time and protecting the nanoparticle from the attack of reticuloendothelial system (RES) and macrophages.

The present invention also provides a preparation method of a water-soluble nanoparticle for delivering an anticancer agent containing hydrophobic core which includes the following steps:

1) Methoxy poly (ethylene glycol) p-nitrophenyl carbonate (MPEG p-NP) is added to a water-soluble chitosan to form amide bond and the by-product, p-nitrophenyl group is eliminated; and 2) Cholesteryl chloroformate is added to the above reaction solution to form another amide bond between free amine group of the water-soluble chitosan and cholesteryl chloroformate.

p-nitrophenyl group, the by-product of the step 1), is eliminated by dialysis with ice water, and the remaining by-product is completely eliminated by purifying with anhydrous ethanol.

In the present invention, in order to produce a water-soluble chitosan nanopaclitaxel having a cancer treating effect, a hydrophilic group methoxy poly (ethylene glycol) p-nitrophenyl carbonate (MPEG p-NP) and a hydrophobic group cholesteryl chloroformate were combined with free amine group of a water-soluble chitosan, resulting in a water-soluble chitosan nanoparticle. Then, paclitaxel was effectively enveloped with the nanoparticles, resulting in a water-soluble chitosan nanopaclitaxel (WSC-NPT) that could be easily re-dispersed in water.

More precisely, the water-soluble chitosan nanopaclitaxel can be produced as follows. In the first step, methoxy poly (ethylene glycol) p-nitrophenyl carbonate (MPEG p-NP) is added to a water-soluble chitosan to form amide bond, and the by-product 'p-nitrophenyl group' is eliminated by dialysis with ice water for 48 hours. The remaining by-products are completely eliminated by purifying the reaction solution with anhydrous ethanol. In the next step, cholesteryl chloroformate is added to the above reaction solution to form another amide bond between free amine group and cholesteryl chloroformate, resulting in a water-soluble chitosan nanoparticle having hydrophobic core (see Scheme 1). Lastly, an anticancer agent (paclitaxel) is given to the above reaction solution, then, the agent is enveloped in cholesterol, a hydrophobic group of the above water-soluble chitosan nanoparticle, leading to the production of water-soluble chitosan nanopaclitaxel.

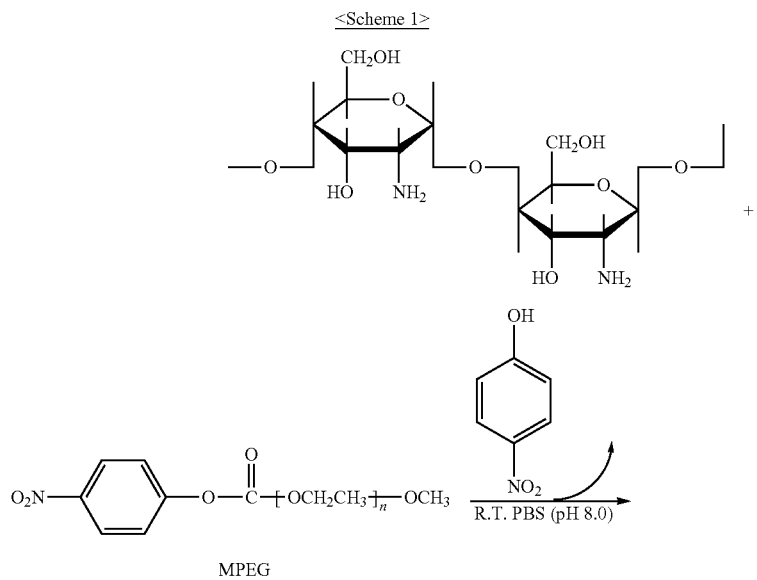

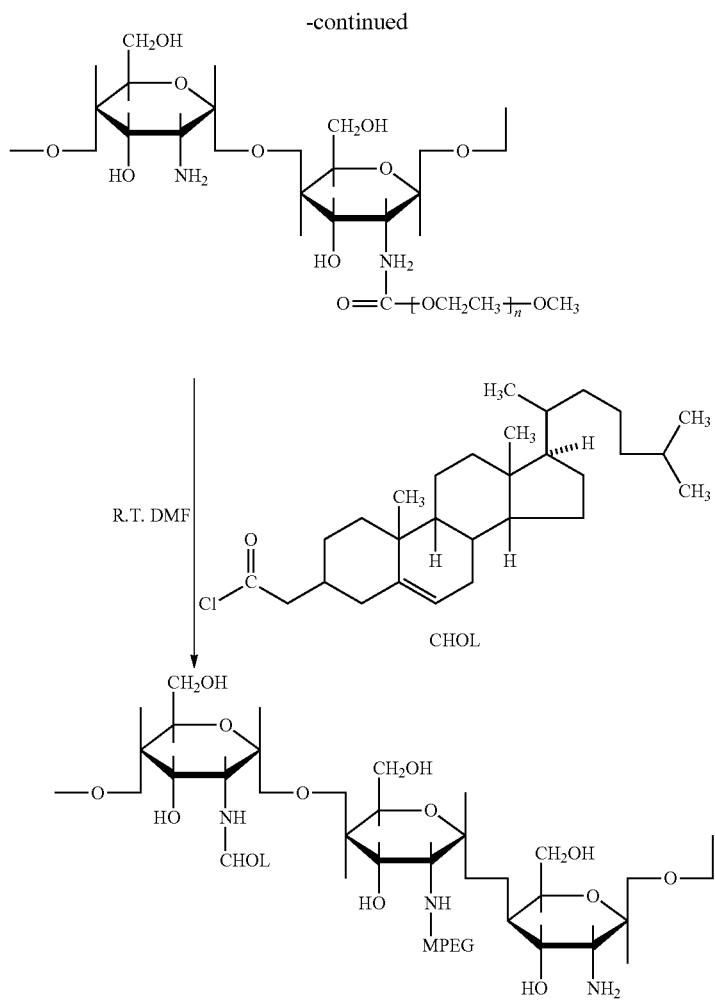

Water-soluble chitosan used in the present invention as an anticancer agent carrier is adequate to deliver an anticancer agent because it contains a highly reactive free amine group.

Unlike other preparation methods using organic solvents which are harmful to human, the preparation of a water-soluble chitosan nanoparticle of the present invention is carried out in PBS (Phosphate Buffered Saline) solution (pH 7.0~8.0) under mild conditions, suggesting the processes are safe and simple.

It is generally known that a polymeric drug is accumulated more in tumor cells than in normal cells owing to its EPR (enhanced permeability and retention effect). A water-soluble chitosan nanoparticle prepared in the present invention using a water-soluble chitosan is also accumulated more in tumor cells than in normal cells, comparing to other conventional anticancer agent carriers, suggesting its excellent anticancer effect. In general, cancer cells are a little more acidic than neighboring cells. A water-soluble chitosan having 6.5 pKa is stabilized better in weak acid, indicating that it is able to target on cancer cells rather than normal cells. Therefore, the water-soluble chitosan nanoparticle is accumulated more in cancer cells.

Water-soluble chitosan nanopaclitaxel containing paclitaxel therein is characterized by excellent re-dispersion force in distilled water after being freeze-dried and also has other merits of natural polymeric materials like a water-soluble chitosan.

Exemplary, non-limiting embodiments of the present invention will now be described more fully hereinafter. This invention may, however, be embodied in many different forms and should not be construed as limited to the exemplary embodiments set forth herein.

EXAMPLE 1

Preparation of a Water-soluble Chitosan Nanoparticle 1

A water-soluble chitosan with molecular weight of 18 kDa and degree of deacetylation of 87% was supplied from KIT-TOLIFE Co. Ltd. Methoxy poly (ethylene glycol) p-nitrophenyl carbonate (MPEG p-NP)), hydrophilic moiety, was purchased from Sigma Co. and cholesteryl chloroformate, hydrophobic group, was purchased from Aldrich Co. Dialysis tubing (MWCO 12,000) was commercially obtained from Spectrum Co. All other chemicals were reagent grade and used as received.

Preparation of a water-soluble chitosan nanoparticle was carried out in the following steps. In step 1, 0.1 g of water-soluble chitosan was dissolved in 15 ml of PBS (pH 7.0~8.0), followed by stirring for one hour. 0.5 g of Methoxy poly (ethylene glycol) p-nitropheyl carbonate (MPEG p-NP) was dissolved in PBS (pH 8.0), which was dropped slowly to the above chitosan reaction solution while the solution was stirring. Two hours later, the solution was dialyzed using a molecular cut-off 12,000 g/mol dialysis tube against cold distilled water for 48 hours, resulting in the formation of a clear product in supernatant and by-product in precipitation layer. Those products were separated and a clear supernatant layer was freeze-dried.

A white product obtained through freeze-drying in the above step 1 was dissolved in 15 ml of PBS (pH 7.0~8.0), followed by stirring for one hour. Cholesteryl chloroformate was dissolved in 1~2 ml of anhydrous DMF by 1.0 per 10 chitosan glucose amine monomers. The cholesteryl chloroformate solution was slowly dropped into the above reaction solution while the reaction solution was stirring for 2 hours. Upon completing the reaction, dialysis was performed with distilled water for 24 hours. Centrifugation was then performed at 10,000 rpm for 10 minutes, followed by filtering with 0.45 μm syringe filter and freeze-drying. A final product, a white water-soluble chitosan nanoparticle, was obtained.

EXAMPLE 2

Preparation of a Water-soluble Chitosan Nanoparticle 2

A water-soluble chitosan nanoparticle was prepared by the same method as described in the above Example 1 except that 1.5 cholesteryl chloroformate per 10 chitosan glucose amine monomers were used.

EXAMPLE 3

Preparation of a Water-soluble Chitosan Nanoparticle 3

A water-soluble chitosan nanoparticle was prepared by the same method as described in the above Example 1 except that 1.8 cholesteryl chloroformate per 10 chitosan glucose amine monomers were used.

EXAMPLE 4

Preparation of a Water-soluble Chitosan Nanopaclitaxel 1

25 mg of water-soluble chitosan nanoparticle prepared in the above Example 1 was dispersed in 10 ml of PBS (pH 7.4), followed by stirring at 40☐ for 30 minutes. 4 mg of paclitaxel was dissolved in 2 ml of ethanol, which was slowly dropped into the above solution, during which sonication was performed using a water type sonicator. Sonication with the above solution was performed by using a bar type sonicator again for 2 seconds, which was repeated 10 times. Dialysis was performed in PBS (pH 7.4). On the next day, dialysis was performed again in distilled water for 12 hours, followed by centrifugation. Then, the product was filtered by 0.45 μm syringe filter and freeze-dried, resulting in a water-soluble chitosan nanopaclitaxel containing paclitaxel therein.

EXAMPLE 5

Preparation of a Water-soluble Chitosan Nanopaclitaxel 2

Water-soluble chitosan nanopaclitaxel was prepared by the same method as described in the above Example 4 except that WSC-NP prepared in the above Example 2 was used.

EXAMPLE 6

Preparation of a Water-soluble Chitosan Nanopaclitaxel 3

Water-soluble chitosan nanopaclitaxel was prepared by the same method as described in the above Example 4 except that WSC-NP prepared in the above Example 3 was used.

EXPERIMENTAL EXAMPLE 1

MTT Assay

MTT assay was performed to investigate toxicity of a water-soluble chitosan used in the present invention. 293T cells were put in a 96 well plate by $5 \times 10^4$ cells/well, followed by culture for 24 hours.

Water-soluble chitosans having different weight average molecular weight (Mw) (10,000, 20,000 and 50,000, respectively) were added to each well by the concentration of 0.1~100 μg/ml, followed by culture at 37☐ for 4 hours. 50 μl of MTT prepared at the concentration of 3 mg/ml was added thereto, followed by further culture at 37☐ for 4 hours. Supernatant was removed. 100 μl of DMSO was put in each well of a 96 well plate, which was left for 10 minutes. Then, micro plate reader (VERSA MAX) was used to investigate the results. Cell viability was calculated by the following Formula 1.

Cell viability(%)=(OD$_{570}$(sample)/OD$_{570}$(control))× 100     <Formula 1>

OD$_{570}$(sample) means the value of OD measured in wells treated with water-soluble chitosan and OD$_{570}$(control) means the value of OD measured in wells treated with PBS buffer solution only. The test results are presented in FIG. 1. As shown in FIG. 1, a water-soluble chitosan having weight average molecular weight ranging from 10,000 to 50,000 has no toxicity.

EXPERIMENTAL EXAMPLE 2

Measurement of FT-IR and $^1$H-NMR Spectroscopy

In order to identify the synthesis of water-soluble chitosan nanoparticle prepared in the above Example 1 modified with hydrophobic group and hydrophilic group, FT-IR (Shimadzu, FT-IR 8700) and $^1$H-NMR spectrometer (Bruker, DRX-500 MHz) were used. For $^1$H-NMR measurement, water-soluble chitosan nanoparticle was dissolved in CDCl$_3$ at the concentration of 10 mg/ml and the spectra were performed at 298 K. To investigate the structural characteristics of the water-soluble chitosan nanoparticle prepared in the above Example 1, $^1$H-NMR spectra were measured in CDCl$_3$ and D$_2$O. The results are presented in FIG. 2 and FIG. 3.

Figure 2B:
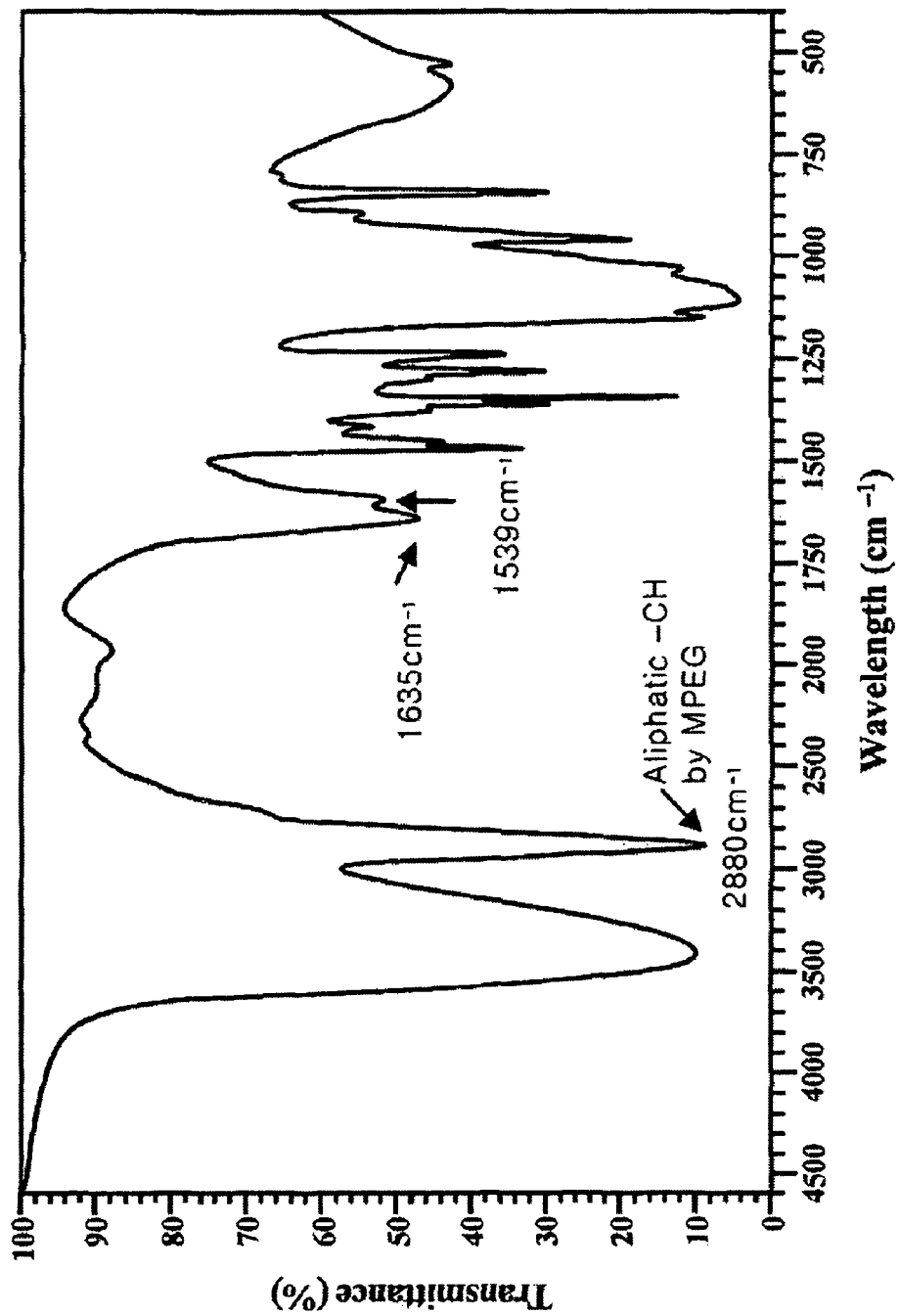

FIG. 2(a) shows the FT-IR spectrum of water-soluble chitosan, in which peaks of amine group and amide group of glucose amine monomer were clearly shown differently at 1539 cm$^{-1}$ and 1635 cm$^{-1}$, respectively. As shown in FIG. 2(b), the introduction of MPEG into a water-soluble chitosan resulted in that a specific peak by aliphatic-CH of MPEG was observed near 2880 cm$^{-1}$, the intensity of amine peak near 1539 cm$^{-1}$, one of specific peaks of a water-soluble chitosan, was reduced by amide bond between free amine group of a water-soluble chitosan and carbonyl group of MPEG, and the intensity of specific peak of amide was increased, comparing to that of amine group, by a new amide bond between a water-soluble chitosan and MPEG. So, the results indicate that MPEG was successfully conjugated in a water-soluble chitosan.

Figure 3A:
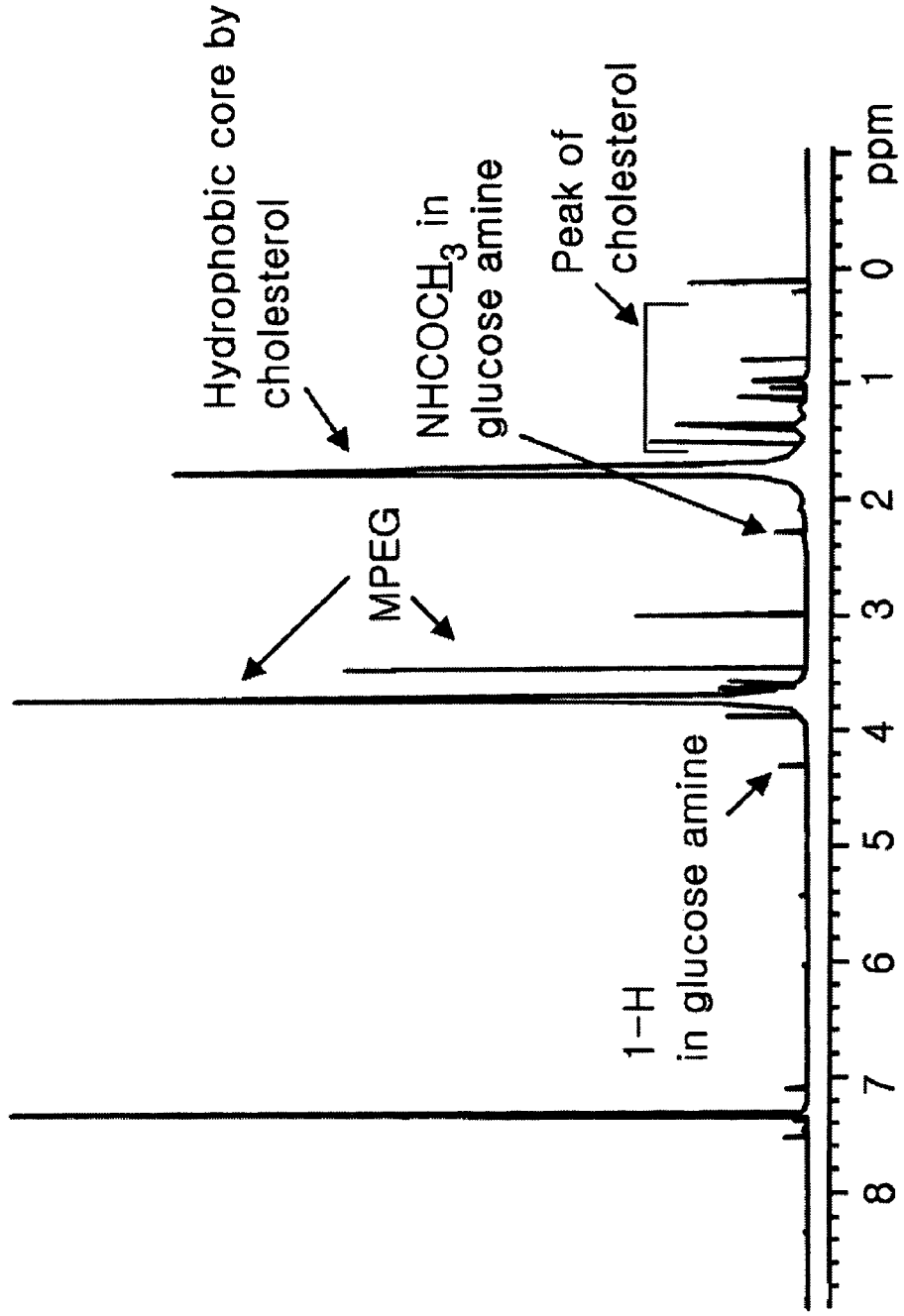
FIGS. 3A, 3B and 3C are a set of graphs showing the IH-NMR spectrum of a WSC wherein a hydrophilic group MPEG p-NP and a hydrophobic group cholesteryl chloroformate are conjugated.
Figure 3B:
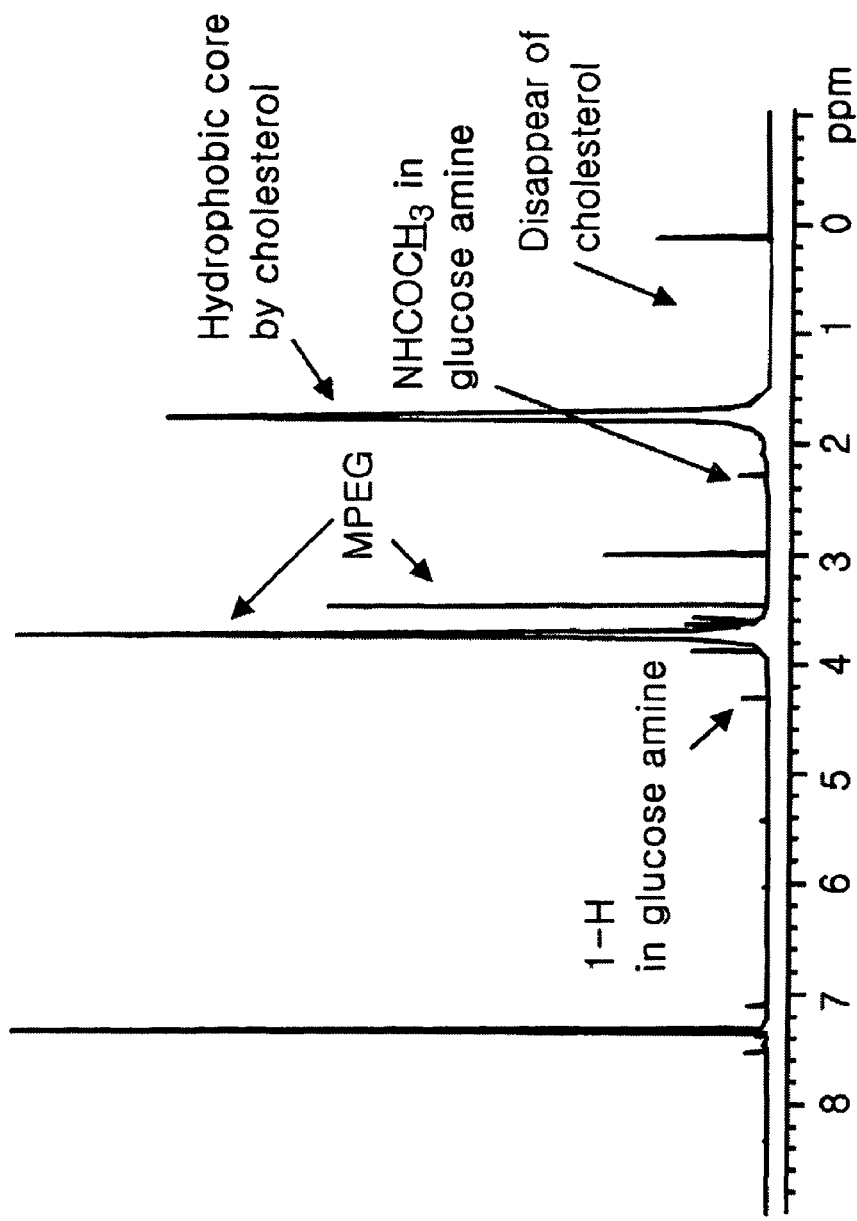
Figure 3C:
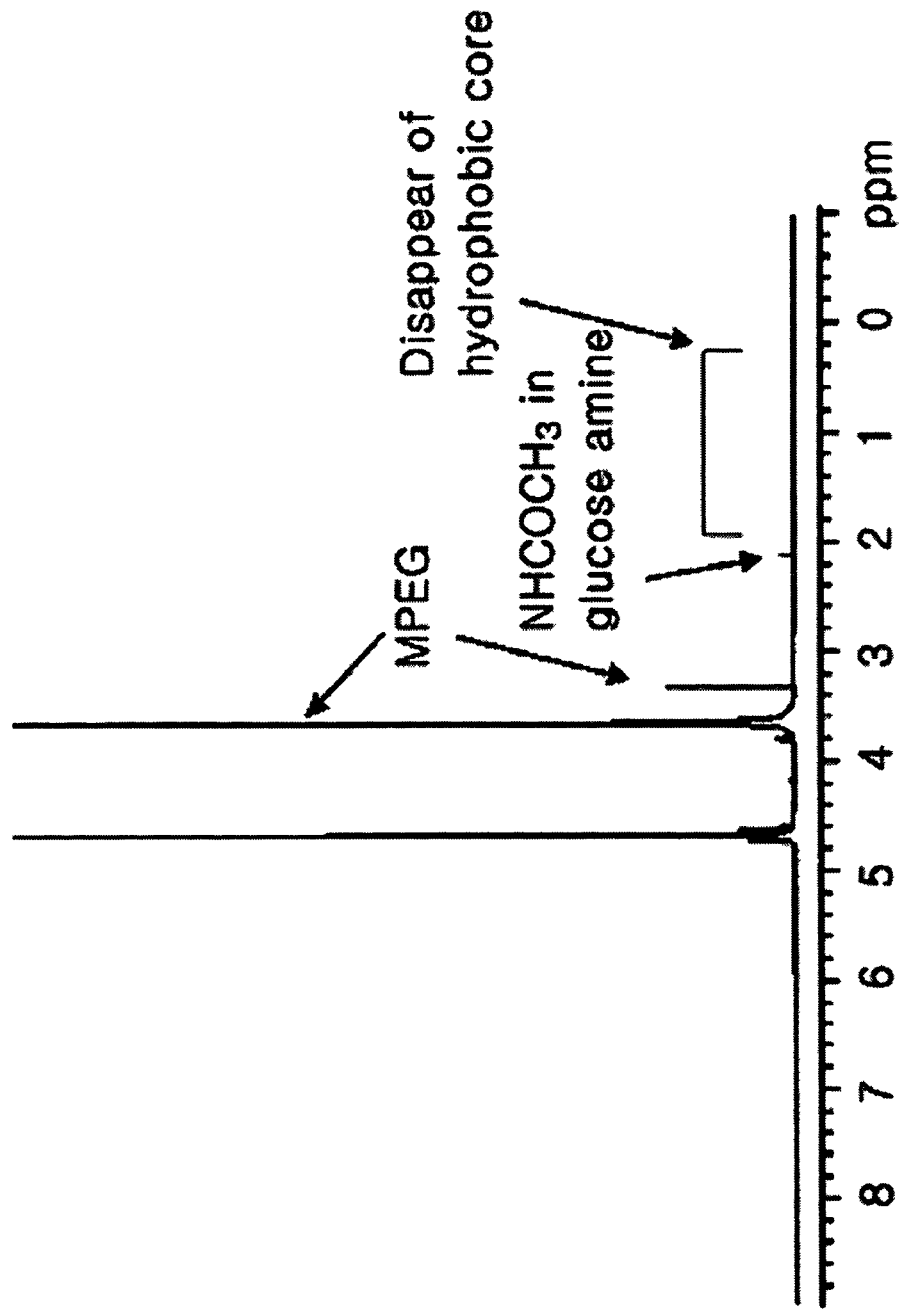

FIG. 3 shows $^1$H-NMR spectrum of a water-soluble chitosan modified with a hydrophilic group MPEG and a hydrophobic group cholesterol. In particular, FIG. 3(a) shows a spectrum showing peaks of cholesterol not reacted around 1.5~0.5 ppm, which was taken after dissolving WSC-NP in CDCl$_3$ without removing the remaining cholesterol. Especially the strong peak observed at the region of 1.8 ppm suggested that hydrophobic core was formed by the linkage of cholesterol, a hydrophobic group, to a chain of a water-soluble chitosan. That is, the original peak of hydrophobic cholesterol was hindered by the bond of polymeric chains of a water-soluble chitosan and MPEG, so that those cholesterols formed a hydrophobic core at 1.8 ppm, making a strong characteristic peak of cholesterol there. FIG. 3(b) shows $^1$H-NMR spectrum of WSC-NP, which was taken after purifying the particle with ethyl ether to eliminate the remaining cholesterol not reacted. As shown in the graph, the peak of cholesterol at 1.5~0.5 ppm disappeared and a specific peak at 1.8 ppm was clearly shown, meaning that the hydrophobic core was formed. FIG. 3(c) shows $^1$H-NMR spectrum obtained after dissolving water-soluble chitosan nanoparticle in D$_2$O, which also confirmed that the hydrophobic core was formed in WSC-NP. As shown in the graph, the specific peak by cholesterol completely disappeared and only characteristic peaks of a water-soluble chitosan and MPEG were observed, supporting that the hydrophobic core was formed. All the above results indicate that MPEG and cholesterol were successfully linked to the chains of a water-soluble chitosan.

EXPERIMENTAL EXAMPLE 3

Morphology Observation of Water-soluble Chitosan Nanoparticle

Figure 5:
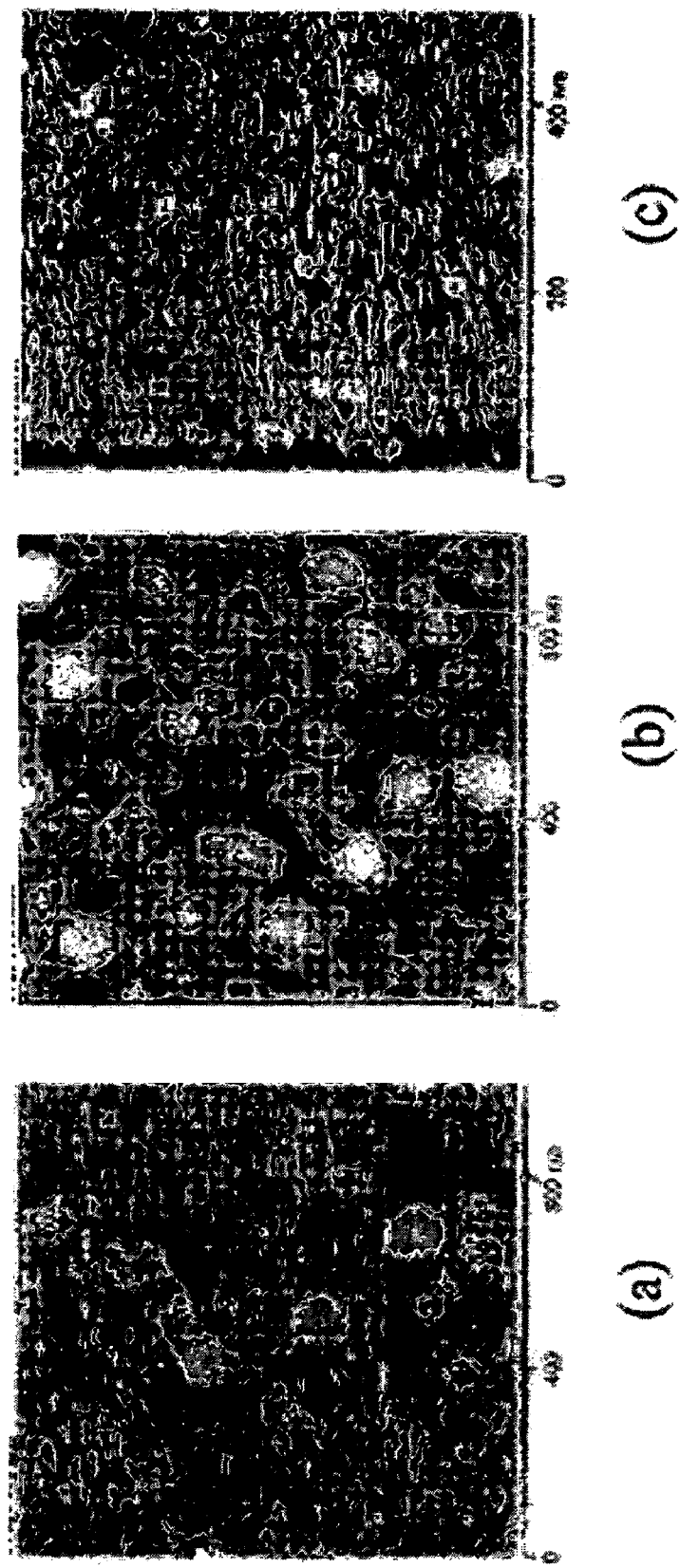

Morphology of WSC-NP of the present invention was examined with TEM (transmission electron microscope; JEOL JEM-2000 FX-II) and AFM (atomic force microscope; PARK's Science Autoprobe CP). A drop of chitosan nanoparticles suspended in 0.01% of phosphotungstic acid (PTA) was placed on a carbon film coated on a copper grid for TEM. For analysis of the AFM image, chitosan nanoparticles of 0.1 mg/ml in distilled water were placed on a silicon water surface and observed at room temperature with cantilever frequencies oscillating between 12 and 24 kHz. FIG. 4 shows the configuration of the surface of water-soluble chitosan nanoparticle investigated by TEM. FIG. 4 shows TEM photographs of water-soluble chitosan nanoparticle. As shown in these photographs, the shape of the water-soluble chitosan nanoparticle was spherical and the sizes were ranged from about 30~150 nm in diameter. When the MPEG ratio to glucosamine unit is constant, the more increase the ratio of cholesterol, the smaller size of chitosan nanoparticle due to the increase of hydrophobicity. FIG. 5 shows AFM observation of water-soluble chitosan nanoparticle. In these photographs, it was confirmed that the water-soluble chitosan nanoparticle had spherical smooth surface and the size of the particle decreased with the increase of substitution with cholesterol, a hydrophobic group, because the particles were densified by cholesterol, which was the same result as obtained from TEM analysis.

EXPERIMENTAL EXAMPLE 4

Photon Correlation Spectroscopy (PCS) Measurement

Photon correlation spectroscopy (PCS) was measured with a Zetasizer 3000 (Malvern instruments, England) with He—Ne laser beam at a wavelength of 633 nm for the determination of surface charge of the WSC-NP of the present invention. The results are presented in Table 1.

TABLE 1

| WSC-NPs | Composition Ratio (WSC:MPEG:Chol) | Particle Size (nm) | CAC (mol) | Zeta Potential (mV) |
| --- | --- | --- | --- | --- |
| Example 1 | 10:2:1.0 | 100~150 | 1.0 × 10$^{-5}$ | 22.4 |
| Example 2 | 10:2:1.5 | 50~100 | 0.6 × 10$^{-5}$ | 18.2 |
| Example 3 | 10:2:1.8 | 30~70 | 0.4 × 10$^{-5}$ | 15.3 |

Water-soluble chitosan was modified with MEPG, a hydrophilic group, and cholesterol, a hydrophobic group, to envelope paclitaxel, a hydrophobic anticancer agent. As shown in Table 1, the size of the particle decreased with the increase of substitution with cholesterol and critical aggregation concentration (CAC) was also reduced. The result indicates that the nanoparticles are formed even in the low concentration when the level of cholesterol, a hydrophobic group, is increased. As a result of Zeta potential measurement, it was confirmed that a positive charge of a water-soluble chitosan was decreased by the substitution of amine group with MPEG and cholesterol.

EXPERIMENTAL EXAMPLE 5

Differential Scanning Calorimetry (DSC) Measurement

Figure 6A:
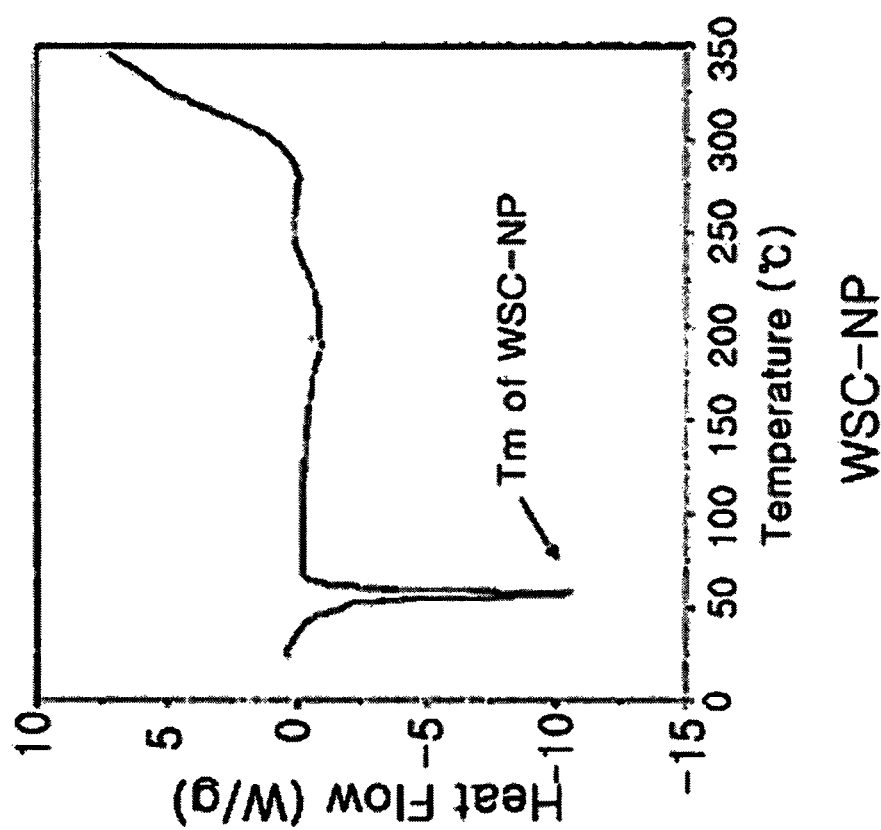
FIG. 6 is a set of graphs showing the results of heat analysis before enveloping paclitaxel (FIG. 6(a)) and after enveloping paclitaxel (FIG. 6(b))
Figure 6B:
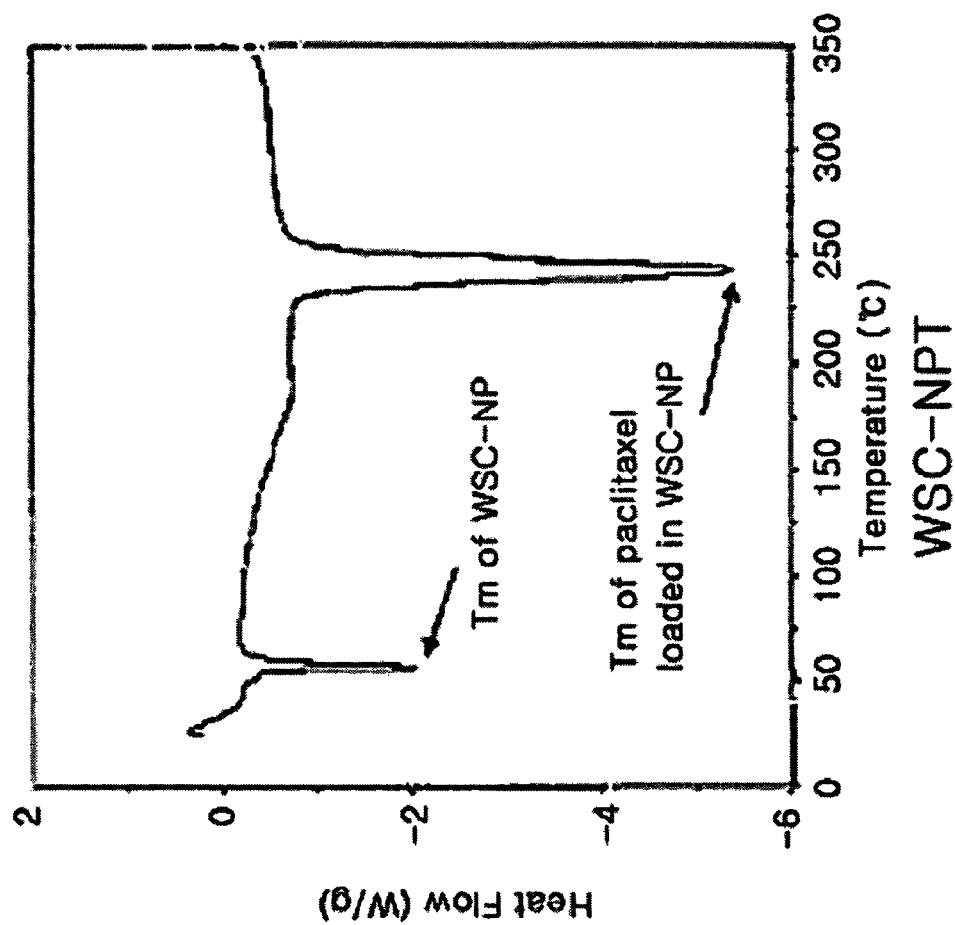

Tm of paclitaxel and a water-soluble chitosan nanopaclitaxel were measured using a TA instrument (Dupont, TA 2000) under nitrogen current. The scanning speed was 10□/min and the range was determined as 20~350□. The results are presented in FIG. 6. FIG. 6 shows the results of heat analysis before (FIG. 6(a)) and after enveloping paclitaxel (FIG. 6(b)). In general, Tm of water-soluble chitosan nanoparticle and paclitaxel was detected at 50□ and 215□ respectively. Tm of WSC-NP not containing paclitaxel therein was detected at around 50□ (see FIG. 6(a)). In the meantime, in the case of a water-soluble chitosan nanopaclitaxel in which paclitaxel was enveloped already, Tm of WSC-NP was detected at around 50□ and at the same time Tm of paclitaxel was seen at around 240□ (see FIG. 6(b)). Tm of paclitaxel contained in a water-soluble chitosan nanopaclitaxel was higher than that of original paclitaxel (215□), which might be because that paclitaxel was completely enveloped in the hydrophobic core of water-soluble chitosan nanoparticle.

EXPERIMENTAL EXAMPLE 6

HPLC Measurement to Quantify the Enveloped Paclitaxel

Paclitaxel enveloped in a water-soluble chitosan nanopaclitaxel prepared in the above Example 4 was quantified by HPLC using phenomenex sphereclone 5 micro ODS(2) 250× 4.6 mm column and 75% methanol as a moving phase. At that time, the flow rate was set to 1.5 ml/min and the temperature was 50☐. And UV detector (226 nm) was used for the measurement. Paclitaxel was dissolved in ethanol, making 20 µl for injection. The results are presented in Table 2.

TABLE 2

| WSC-NPT | Composition Ratio (WSC:MPEG:Chol) | Loading Content (wt. -%) | Loading Efficiency (wt. -%) |
| --- | --- | --- | --- |
| Example 4 | 10:2:1.0 | 4.4 | 13 |
| Example 5 | 10:2:1.5 | 10 | 13 |
| Example 6 | 10:2:1.8 | 18 | 26 |

Table 2 shows loading content and loading efficiency of enveloped paclitaxel in a water-soluble chitosan nanopaclitaxel prepared in the above Example 4~Example 6. The loading content and the loading efficiency of paclitaxel were increased with the increase of substitution with cholesterol, a hydrophobic group, in the chains of a water-soluble chitosan harboring MPEG. And the results were confirmed again by the quantification by HPLC as shown in FIG. 7.

Figure 7A:
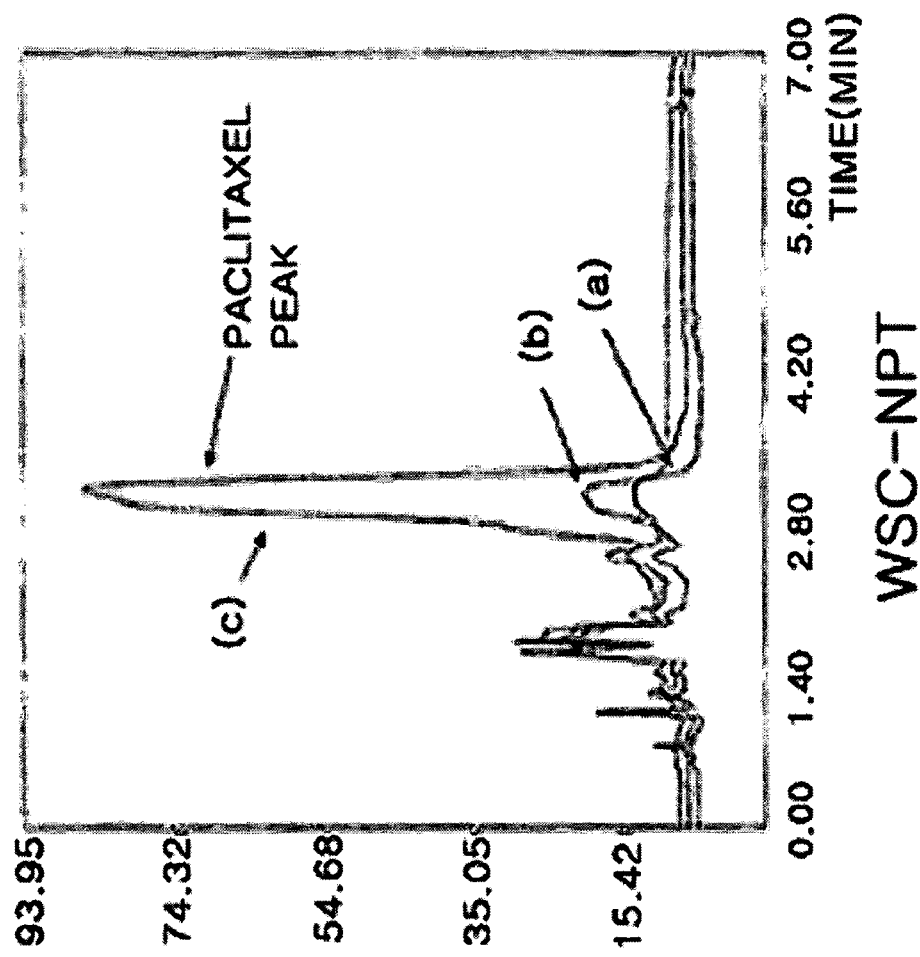
FIGS. 7A and 7B are a set of graphs showing the results of mass analysis of both paclitaxel enveloped in a WSC-NPT and a standard paclitaxel.
Figure 7B:
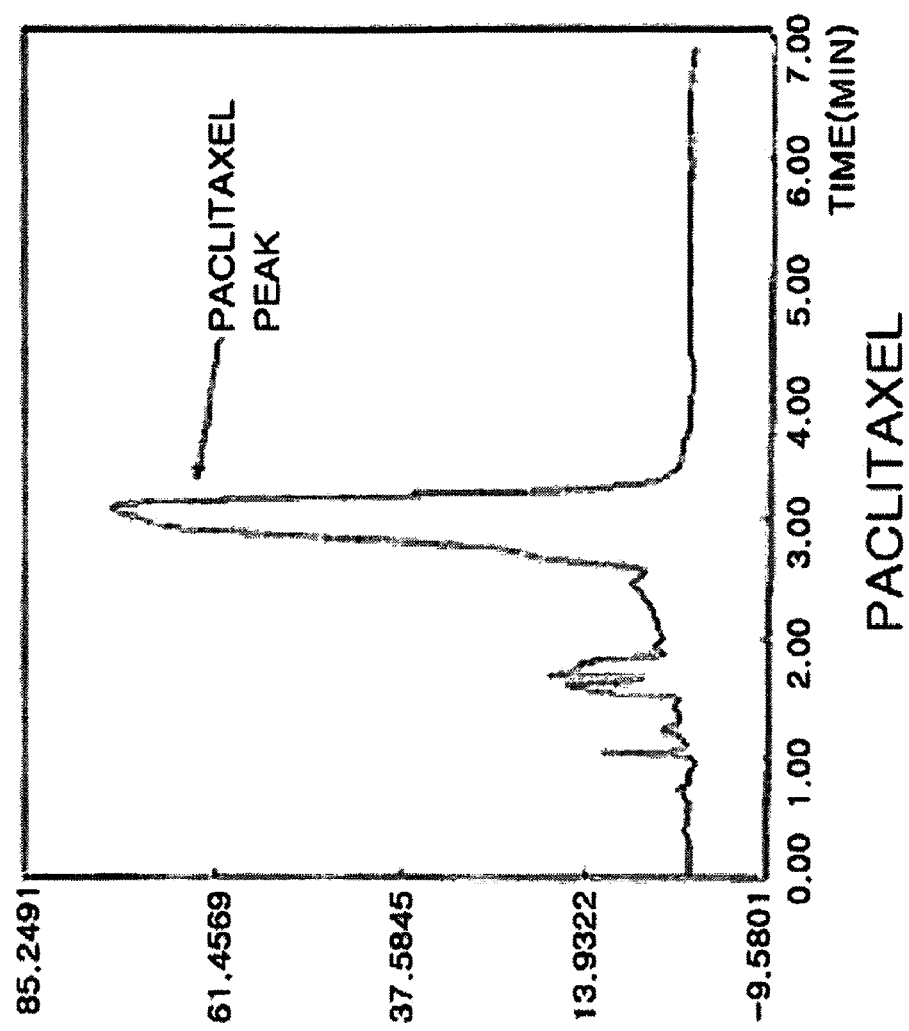

As shown in FIG. 7, characteristic peak of paclitaxel(b) was detected at 3.4 min and (a) shows the quantified paclitaxel enveloped in a water-soluble chitosan nanopaclitaxel. The results indicate that the loading content of paclitaxel was increased with the increase of cholesterol content, which was resulted from the hydrophobic interaction between water-soluble chitosan nanoparticle and cholesterol.

EXPERIMENTAL EXAMPLE 7

Anti-tumor Efficacy in a Tumor Induced CT-26 Mouse Model

Female BALB/c mice (average weight: 20 g) were injected subcutaneously in the flank with CT-26 mourine tumor cells ($5 \times 10^4$ cells/mouse). When the tumor was growing to the size of 3 mm×3 mm, the mice were divided into two groups; an experimental group and a control group. Each group was filled with 8 mice having a tumor and they were marked in their ears for the observation. 15 days after the transplantation, the administration (an intravenous injection) of drug and vehicle began. Each test drug was administered both with low dose of 2 mg/kg and with high dose of 10 mg/kg every three days four times total for 12 days. Only vehicle (cremophor: dehydrated ethyl alcohol, 1:1 v/v) was administered to a control group. Death rate of mice was checked every day and the growth of a tumor was measured using caliper measurement device at two or three day interval. Tumor volume was calculated by the following Formula 2.

$$\text{Tumor volume: mm}^3 = (\text{Length} \times \text{Width}^2)/2 \qquad \text{<Formula 2>}$$

Figure 8:
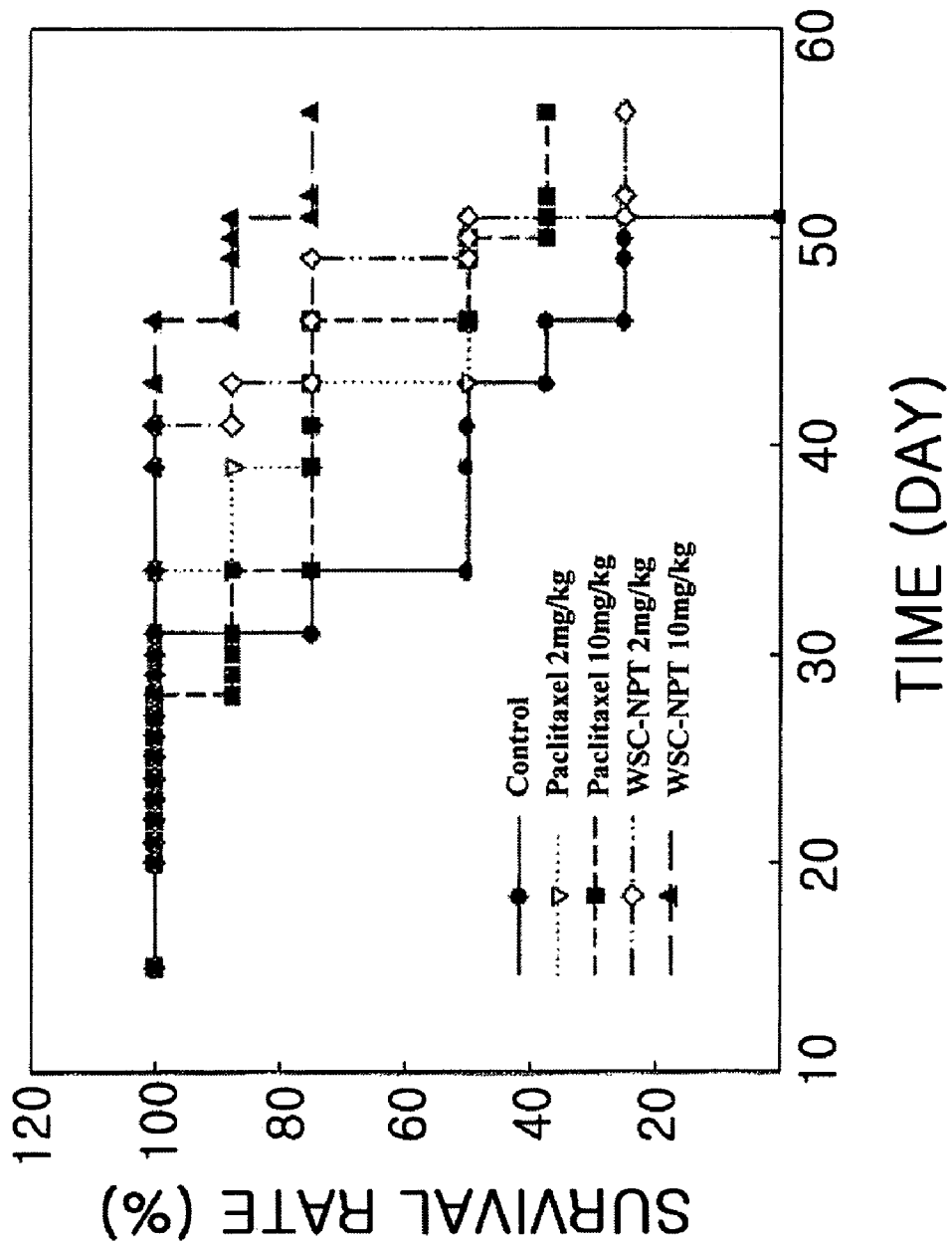
FIG. 8 is a graph showing the survival rate of mice according to the treatment of different drugs.

A drug or a vehicle was injected into tail vein of a mouse two weeks after tumor transplantation. FIG. 8 is a graph showing the survival rate of mice each administered with paclitaxel and a water-soluble chitosan nanopaclitaxel. Control group mice lost their lives faster than any other group. Mice administered with high dose (10 mg/kg) died much earlier within 40 days than three other groups, but the survival rates of three groups each treated with 2 mg/kg and 10 mg/kg of paclitaxel and 2 mg/kg of a water-soluble chitosan nanopaclitaxel were not much different from each other. An experimental group treated with high dose (10 mg/kg) of a water-soluble chitosan nanopaclitaxel showed the highest survival rate among groups during the whole period of experiments.

Figure 9:
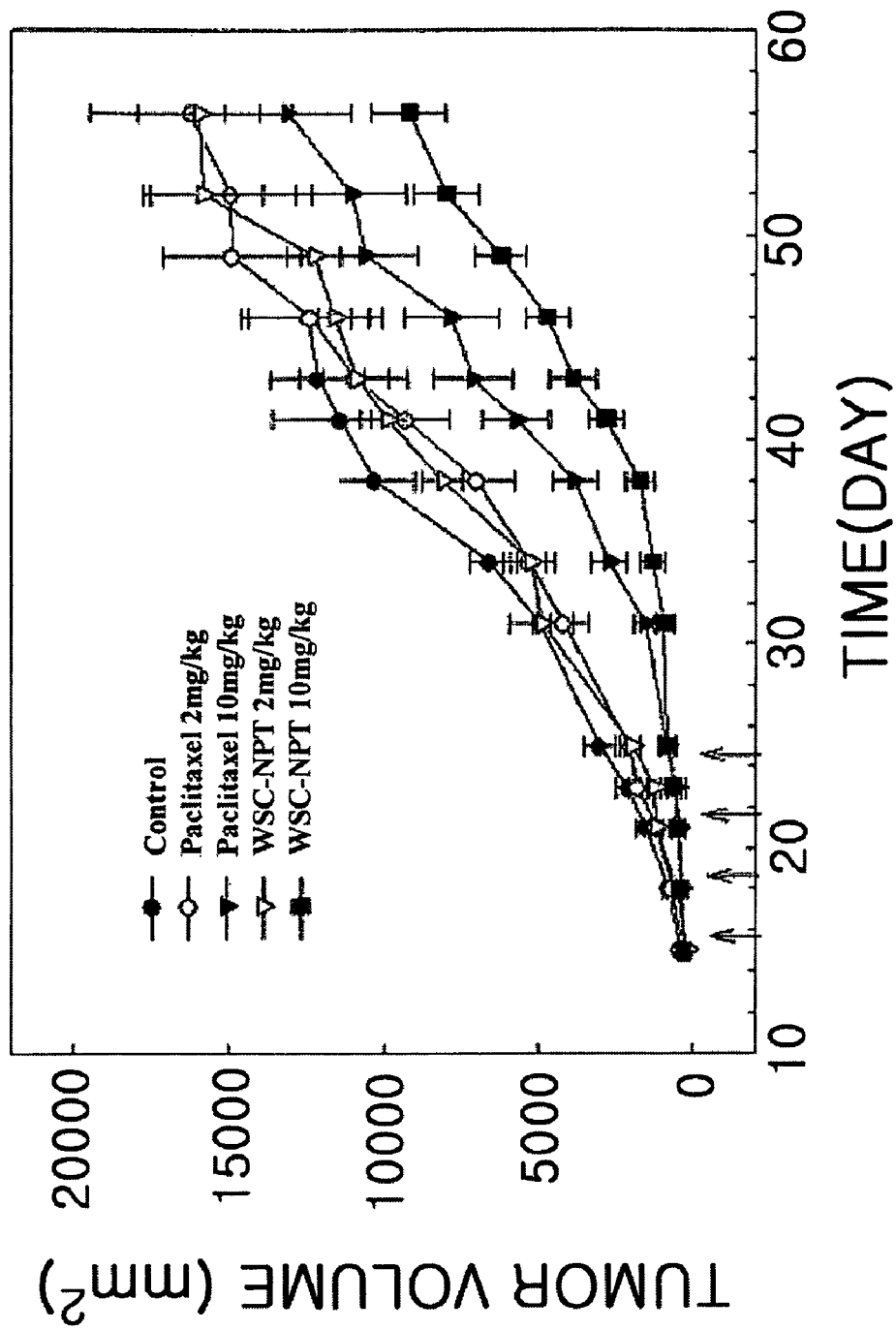
FIG. 9 is a graph showing the growth of a tumor after the administration of a drug to a mouse.

FIG. 9 is a graph showing the anticancer activities of paclitaxel and a water-soluble chitosan nanopaclitaxel to CT-26 tumor models. Tumor volume was measured from the 15$^{th}$ day after tumor cell transplantation. When the two samples, paclitaxel and a water-soluble chitosan nanopaclitaxel, were administered with low dose of 2 mg/kg, the tumor volume was not much different between them. However, when the drugs were administered with high dose of 10 mg/kg, the tumor volume in mice treated with paclitaxel was remarkably decreased, comparing to other groups each treated with vehicle only, 2 mg/kg of paclitaxel and 2 mg/kg of a water-soluble chitosan nanopaclitaxel. When paclitaxel was administered with 10 mg/kg, the growth of a tumor was excellently inhibited, but 30 days later the tumor began growing again. As shown in FIG. 9, the anticancer activity of a water-soluble chitosan nanopaclitaxel was the highest with the dose of 10 mg/kg. When a water-soluble chitosan nanopaclitaxel was administered, the tumor growth was constantly inhibited up to 38 days but began after 40 days.

Figure 10:
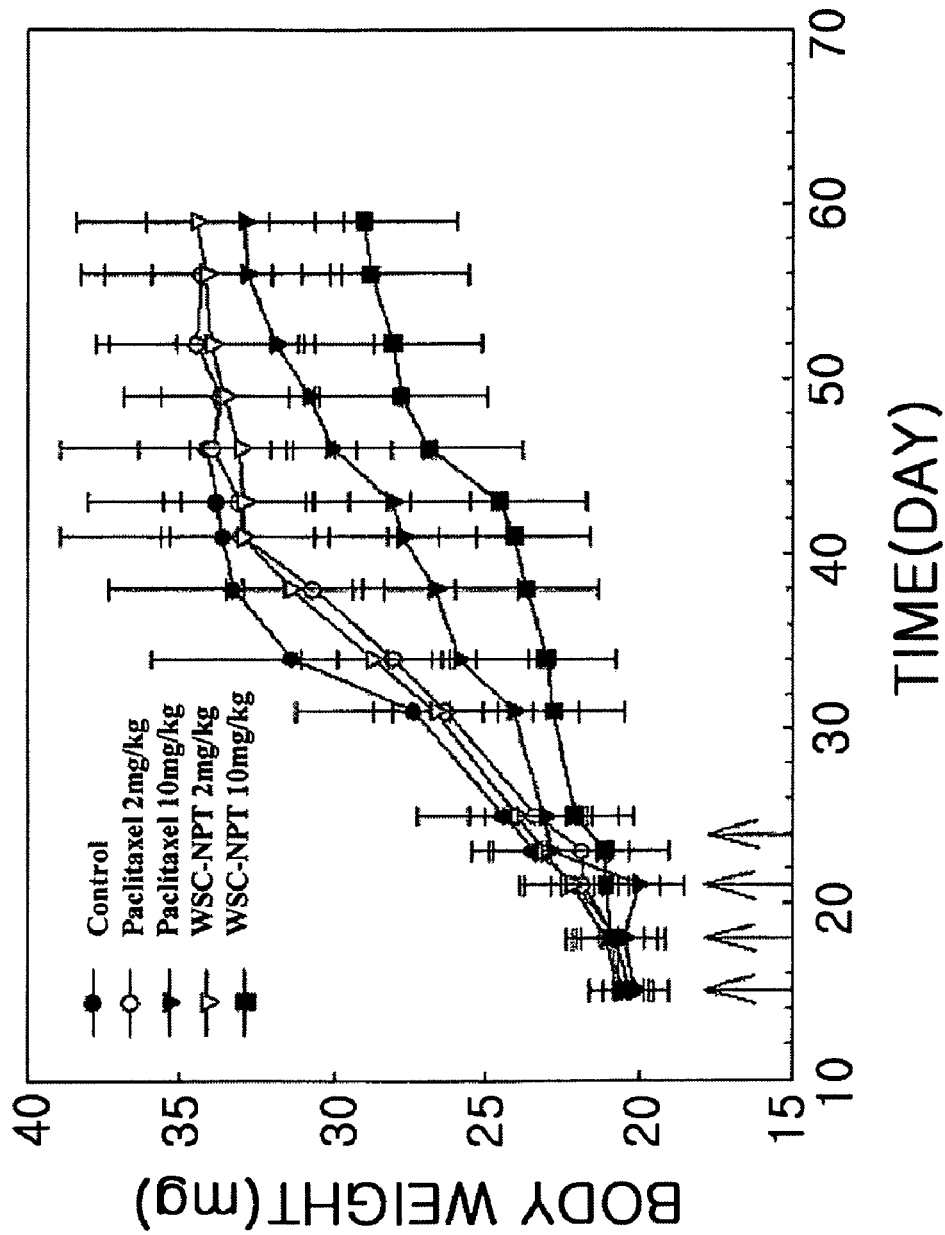
FIG. 10 is a graph showing the weight changes after the administration of a drug of a mouse transplanted with a tumor.

FIG. 10 is a graph showing the weight changes after the administration of a drug to mice transplanted with a tumor. As shown in the graph, weight changes among the groups (control, 2 mg/kg of paclitaxel treating group, 2 mg/kg of a water-soluble chitosan nanopaclitaxel treating group) were not significantly different. Though, the weight of mice treated with high dose of a water-soluble chitosan nanopaclitaxel was greatly decreased. The results indicate that the administration of a water-soluble chitosan nanopaclitaxel with high dose decreases the size of tumor, resulting in the inhibition of weight gaining.

Low dose of a water-soluble chitosan nanopaclitaxel cannot inhibit tumor growth and not affect survival rate much either, but high dose of the drug increases survival rate and decreases tumor volume better than original paclitaxel. In conclusion, high dose over 10 mg/kg of a water-soluble chitosan nanopaclitaxel has an excellent anticancer activity.

As explained hereinbefore, water-soluble chitosan nanoparticle for delivering an anticancer agent of the present invention is useful for the production of a water-soluble chitosan nanopaclitaxel in which an anticancer agent, paclitaxel, is successfully enveloped by introducing a hydrophilic group and a hydrophobic group into the region of highly reactive free amine group by taking advantage of a water-soluble chitosan. The water-soluble chitosan nanopaclitaxel has many advantages of a polymer because it is produced based on a natural polymer 'a water-soluble chitosan'. In detail, it is re-dispersed in distilled water easily after being freeze-dried and is accumulated in tumor cells better than the other anticancer agent carriers. In addition, a water-soluble chitosan is stabilized better in weak acid, so that the particles of the invention target on cancer cells rather than on normal cells, resulting in better accumulation of nanoparticles in cancer cells, indicating that the particles have an excellent anticancer activity.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A chitosan nanoparticle-paclitaxel complex, comprising: a water-soluble chitosan nanoparticle (WSC-NP) and paclitaxel,
   wherein the water-soluble chitosan nanoparticle is spherical and having a hydrophobic core and paclitaxel is enveloped in the water-soluble chitosan nanoparticle to be present in the hydrophobic core,
   wherein the water-soluble chitosan nanoparticle comprises chitosan derivatives with hydrophobic cholesterol groups attached to amino groups of the water soluble chitosan and hydrophilic methoxy poly (ethylene glycol) groups attached to other amino groups of the water soluble chitosan, and
   wherein the water soluble chitosan is prepared by the method comprising:
   a) enzymatically hydrolyzing an organic or inorganic acid salt of a chitosan oligosaccharide;
   b) reacting the hydrolysis product of step (a) with trialkylamine;
   c) adding an organic solvent to the product of step (b) to remove a trialkylamine salt at the C2-position of the chitosan oligosaccharide;
   d) adding an inorganic acid to the product of step (c) to remove a trialkylamine salt at the C-6 position of the chitosan oligosaccharide; and
   e) purifying the chitosan from the product of step (d) to obtain a chitosan with free amine groups and having a molecular weight ranging from 10,000 to 50,000 Da,
   wherein the number ratio of glucose amine monomers of water-soluble chitosan:methoxy poly (ethylene glycol): cholesterol is 10:2:1.8,
   wherein the size of the water-soluble chitosan nanoparticle ranges from 30 to 150 nm, and
   wherein the chitosan nanoparticle-paclitaxel complex is prepared by the method comprising:
   1) adding MPEG to the water-soluble chitosan, thereby forming an amide bond;
   2) eliminating the p-nitrophenyl groups, by-products of step 1), by dialysis with ice water, and completely eliminating the remaining by-products by purifying with anhydrous ethanol;
   3) adding cholesteryl chloroformate to the above reaction solution to form another amide bond between free amine group of the water-soluble chitosan and cholesteryl chloroformate; and
   4) adding paclitaxel to the product of step 3) while sonicating,
   wherein the steps 1)-4) are performed in Phosphate Buffered Saline (PBS) solution.

2. A method of making the chitosan nanoparticle-paclitaxel complex of claim 1 comprising:
   1) adding MPEG to a water-soluble chitosan, thereby forming an amide bond; wherein the water soluble chitosan is prepared by a method comprising:
   a) enzymatically hydrolyzing an organic or inorganic acid salt of a chitosan oligosaccharide;
   b) reacting the hydrolysis product of step (a) with a trialkylamine;
   c) adding an organic solvent to the product of step (b) to remove a trialkylamine salt at the C2-position of the chitosan oligosaccharide;
   d) adding an inorganic acid to the product of step (c) to remove a trialkylamine salt at the C-6 position of the chitosan oligosaccharide; and
   e) purifying the chitosan from the product of step (d) to obtain a chitosan with free amine groups;
   2) eliminating the p-nitrophenyl groups, by-products of step 1), by dialysis with ice water, and completely eliminating the remaining by-products by purifying with anhydrous ethanol;
   3) adding cholesteryl chloroformate to the above reaction solution to form another amide bond between free amine group of the water-soluble chitosan and cholesteryl chloroformate; and
   4) adding paclitaxel to the product of step 3) while sonicating;
   wherein steps 1)-4) are performed in Phosphate Buffered Saline (PBS) solution.

* * * * *